United States Patent [19]

Knifton

[11] 4,362,822

[45] Dec. 7, 1982

[54] PROCESS FOR PREPARING ACETIC AND PROPIONIC ACIDS AND THEIR ESTERS

[75] Inventor: John F. Knifton, Austin, Tex.

[73] Assignee: Texaco Inc., White Plains, N.Y.

[21] Appl. No.: 316,196

[22] Filed: Oct. 29, 1981

[51] Int. Cl.$^3$ .............................................. C07C 27/06
[52] U.S. Cl. .............................. 518/700; 252/431 N; 252/431 P; 518/715
[58] Field of Search .......................................... 518/700

[56] References Cited

U.S. PATENT DOCUMENTS

| | | | |
|---|---|---|---|
| 2,636,046 | 4/1953 | Gresham | 518/715 |
| 4,088,671 | 5/1978 | Kobylinski | 518/715 |
| 4,265,828 | 5/1981 | Knifton | 518/700 |
| 4,315,994 | 2/1982 | Knifton | 518/700 |

*Primary Examiner*—Howard T. Mars
*Attorney, Agent, or Firm*—Jack H. Park; Walter D. Hunter

[57] ABSTRACT

This invention concerns a process for making acetic and propionic acids and their esters which comprises contacting a mixture of CO and $H_2$ at a pressure of about 500 psig or greater and at a temperature of at least about 150° C. with a catalyst system comprising a ruthenium-containing compound and a halogen-containing titanium or zirconium salt dispersed in a low melting quaternary phosphonium or ammonium base or salt.

32 Claims, No Drawings

PROCESS FOR PREPARING ACETIC AND PROPIONIC ACIDS AND THEIR ESTERS

BACKGROUND OF THE INVENTION

1. Field of the Invention

This invention concerns an improved process for preparing acetic and propionic acids and their esters by a single stage reaction of oxides of carbon with hydrogen in presence of a catalyst system.

2. Prior Art

There are ever-increasing efforts to provide new methods of making carboxylic acids such as acetic acid and esters thereof which are particularly useful in preparing a wide variety of organic compounds such as cellulose acetate, vinyl acetate etc. An ever present aim is to prepare such material in relatively high yields directly from carbon monoxide and hydrogen utilizing a catalyst system providing good selectivity.

A number of processes have been described in the literature for manufacturing carboxylic acids and esters from carbon monoxide and alcohols or from carbon monoxide and hydrogen. For example, in U.S. Pat. No. 3,717,670 a method for preparing such carboxylic acids is disclosed in which an alcohol and carbon monoxide are reacted in the presence of a catalyst composition consisting of a rhodium compound and, for example, chromium trioxide. When hydrogen and carbon monoxide are passed over a catalyst comprising rhodium in combination with molybdenum and/or tungsten a reaction product containing acetic acid, acetaldehyde and/or ethanol is formed according to the disclosure of U.S. Pat. No. 4,096,164. A similar method is described in U.S. Pat. No. 4,014,913 where carbon monoxide and hydrogen are reacted in the presence of a rhodium-manganese catalyst. The reaction of carbon monoxide and hydrogen in the presence of rhodium metal catalyst to give a liquid product containing a substantial proportion of acetic acid, ethanol and/or acetaldehyde is disclosed in U.S. Pat. No. 4,246,186. Likewise in U.S. Pat. No. 4,162,262 it is noted that the reaction of hydrogen and carbon monoxide in the presence of a catalyst comprising thorium and/or uranium yields a product containing a large amount of two-carbon atom products. Other processes for preparing carboxylic acids from carbon monoxide and hydrogen are disclosed in U.S. Pat. No. 4,101,450 and in Dutch Pat. Nos. 7,500,910 and 7,500,918.

One serious problem associated with synthesis gas operations in the past has been the non-selectivity of the product distribution since high activity catalysts generally yield a liquid product containing numerous hydrocarbon products and hydrocarbons as well. Thus, complicated recovery schemes are necessary to separate the desired products and the overall yield of the valuable organic products is low. This is a definite need in the art for a process which will produce acetic and propionic acids and their esters in high yield and which does not require the use of an iodine-containing promoter.

This invention therefore is to provide a process of making acetic and propionic acids and esters thereof by resort to a unique bimetallic 'melt' catalyst system which produces said acids and esters in good yields and with excellent selectivity.

SUMMARY OF THE INVENTION

This invention is concerned with a method for making acetic and propionic acids and their esters in a one-stage process which comprises contacting a mixture of CO and $H_2$ at a pressure of about 500 psig or greater and a temperature of at least about 150° C. with a catalyst system comprising a ruthenium-containing compound and a halogen-containing titanium or zirconium salt dispersed in a low melting quaternary phosphonium or ammonium base or salt.

DETAILED DESCRIPTION OF THE INVENTION

Catalysts that are suitable in the practice of this invention contain ruthenium and titanium or zirconium. The catalysts may be chosen from a wide variety of organic or inorganic compounds, complexes, etc., as will be shown and illustrated below. It is only necessary that the catalyst precursor actually employed contain said metals in any of their ionic states. The actual catalytically active species is then believed to comprise ruthenium and titanium or zirconium in complex combination with carbon monoxide and hydrogen. The most effective catalysis is believed to be achieved where ruthenium and titanium or zirconium hydrocarbonyl species are solubilized in a quaternary salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The halogen-containing titanium and zirconium salt catalyst precursors may take many different forms. For instance, suitable halogen-containing titanium or zirconium salts include titanium and zirconium halides such as titanium dichloride oxide, zirconium dichloride oxide, ($ZrOCl_2.4H_2O$); zirconium(IV) bromide, zirconium(IV) chloride, titanium(IV) bromide, titanium(III) chloride and titanium(IV) chloride. Alternatively, the titanium and zirconium halide salts may be in complexed form with other coordinating ligands. Suitable halogen-containing titanium or zirconium complexes include bis(cyclopentadienyl)zirconium dichloride, bis(cyclopentadienyl)zirconium hydrochloride, bis(indenyl)titanium dichloride, cyclopentadienyltitanium trichloride and titanocene dichloride.

Preferred titanium and zirconium halogen-containing salts include bis(cyclopentadienyl)zirconium dichloride, bis(cyclopentadienyl)titanium dichloride and bis(cyclopentadienyl)zirconium hydrochloride.

If desired, in practicing this invention, mixtures of the ruthenium-containing compounds as well as the mixtures of the halogen-containing titanium and/or zirconium salts may be employed.

Preferably, in the practice of this invention, the composition of the catalyst system comprising a ruthenium-containing compound and a halogen-containing titanium or zirconium salt is such that the atomic ratio of total halogen, as derived from the ruthenium-containing compound and the halogen-containing titanium or zirconium salt to the total of Ru+Ti or Zr should not exceed 2:1.

In a second embodiment of the process of this invention acetic and propionic acids and their esters are prepared by contacting a mixture of CO and $H_2$ at a pressure of about 500 psig or greater and at a temperature of at least about 150° C. with a catalyst system comprising a ruthenium-containing compound of the type outlined above, a halogen-free titanium or zirconium compound plus, as a third component, an iodide or iodine compound dispersed in a low melting quaternary phosphonium or ammonium base or salt. In this case, suitable halogen-free titanium or zirconium compounds may include zirconium diacetate oxide, zirconium dinitrate oxide, zirconium(IV) 2,4-pentanedionate, zirconium(IV) i-propoxide, zirconium(IV) n-propoxide, titanium(IV) butoxide, titanium(IV) cresylate, titanium(IV) ethoxide, titanium(IV) methoxide, titanium(IV) n-nonylate, titanium oxalate, titanium(IV) stearylate and titanium oxide. Suitable iodine sources include elemental iodine and organic iodides such as alkyl iodides, acyl iodides and aryl iodides. Examples of suitable organic iodides are alkyl iodides such as methyl iodide, ethyl iodide etc.

Generally, in the practice of this invention, the ruthenium-containing compound and either the halogen-containing titanium or zirconium salt, or the halogen-free titanium or zirconium compound plus source of iodine, are first dispersed in a low-melting quaternary phosphorium or ammonium base or salt prior to their catalytic use in making carboxylic acids. It is interesting to note that the halogen-containing titanium-or zirconium salt alone when dispersed in the low-melting salt or base, has little, if any activity in promoting the manufacture of acetic or propionic acids or their esters from synthesis gas.

The quaternary phosphonium or ammonium base or salt must be relatively low melting, that is, melt at a temperature less than about the temperature of reaction of making aliphatic carboxylic acids. Usually the quaternary compound has a melting point less than about 180° C. and most often has a melting point less than 150° C.

Suitable quaternary phosphonium salts have the formula:

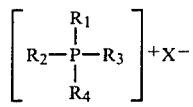

where $R_1$, $R_2$, $R_3$ and $R_4$ are organic radicals, particularly alkyl, aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance. Also useful are the corresponding quaternary ammonium bases and salts in the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetramethylammonium hydroxide, pentahydrate and trimethyldodecylammonium bromide.

The preferred quaternary salts are generally the tetralkylphosphonium salts containing alkyl groups having 1-6 carbon atoms, such as methyl, ethyl, and butyl. Tetrabutylphosphonium salts, such as tetrabutylphosphonium bromide, are most preferred for the practice of this invention. Preferred tetrabutylphosphonium salts or bases include the bromide, chloride, iodide, acetate and chromate salts and hydroxide base.

Generally, in this catalyst system the molar ratio of the ruthenium compound to the quaternary phosphonium or ammonium salt or base will range from about 1:0.01 to about 1:100 or more and, preferably, will be from about 1:0.5 to about 1:20.

The quantity of ruthenium compound employed in the instant invention is not critical and may vary over a wide range. In general, the novel process is desirably conducted in the presence of a catalytically effective quantity of the active ruthenium species and of the titanium or zirconium which gives the desired product in reasonable yield provided the atomic ratio of the total halogen as derived from ruthenium-containing compound and the halogen-containing titanium or zirconcium salt to the total of Ru+Ti or Zr does not exceed 2:1. The reaction proceeds when employing as little as about $1 \times 10^{-6}$ weight percent, and even lesser amounts, of ruthenium together with about $1 \times 10^{-6}$ weight percent or less of titanium or zirconium, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 weight percent in conjunction with a titanium or zirconium concentration of from about $1 \times 10^{-5}$ to about 5 weight percent, based on the total weight of reaction mixture is generally desirable in the practice of this invention.

The temperature range which can usefully be employed in these syntheses is a variable dependent upon other experimental factors, including the pressure, and the concentration and choice of the particular species of the ruthenium catalyst as well as the particular halogen-containing titanium or zirconium salt co-catalyst among other things. The range of operability is from about 150° to about 350° C. when superatmospheric pressure of syngas are employed. A narrow range of about 180° to about 250° C. represents the preferred temperature range.

Superatmospheric pressures of about 500 psig or greater lead to substantial yields of acetic and propionic acids and their esters by the process of this invention. A preferred operating range is from 2000 psig to 9000 psig, although pressures above 9000 psig also provide useful yields of the desired acids and esters.

The relative amounts of carbon monoxide and hydrogen which may be initially present in the syngas mixture are available, and these amounts may be varied over a wide range. In general, the mole ratio of $CO:H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of acetic acid and propionic acid formed during the course of this process include methyl acetate, ethyl acetate, propyl acetate, methyl propionate, ethyl propionate and propyl propionate, etc. These esters and the individual acids formed can be conveniently recovered from the reaction mixture by distillation, extraction, etc.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired acids and esters and said materials may be recovered, as previously pointed out, by methods well known in the art, such as distillation, fractionation, extraction and the like. A fraction rich in the catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

The following examples illustrate various embodiments of this invention and are to be considered not limitative.

EXAMPLE 1

This example illustrates the synthesis of acetic acid in high yield together with propionic acid and their esters directly from synthesis gas using a zirconium-ruthenium containing catalyst dispersed in tetrabutylphosphonium bromide salt (m.p. 100° C.).

A mixture of ruthenium(IV) oxide (4 mmoles) and bis(cyclopentadienyl)zirconium hydrochloride (4 mmoles) dispersed in tetrabutylphosphonium bromide (10.0 g) was charged to a glass liner, under nitrogen purge, and transferred to a 450 ml capacity pressure reactor equipped with heating and means of agitation. The reactor was sealed, flushed with $CO/H_2$ mixture and pressured to 4000 psig with a 1:1 molar $CO/H_2$ mixture. The mixture was heated to 220° C. with rocking, the pressure allowed to rise to ca. 6635 psig, and the reactor held at temperature for 18 hours.

On cooling, the reactor pressure (2425 psig) was noted, a typical gas sample taken and the excess gas removed. A dark-green liquid product (15.8 g) was recovered and samples were analyzed by glc and Karl Fischer titration and following results were obtained:

45.3 wt.% acetic acid
3.2 wt.% propionic acid
9.6 wt.% ethyl acetate
5.6 wt.% ethyl propionate
3.3 wt.% propyl propionate
1.9 wt.% water A small quantity of lighter, water-white, liquid phase was identified as primarily hydrocarbon.

Analysis of typical off-gas samples showed the presence of:

39% hydrogen
23% carbon monoxide
26% carbon dioxide
7% methane

Since the total catalyst charge to the glass liner was 11.8 g, the yield of liquid products was calculated to be:

$$\frac{15.8 - 11.8}{11.8} \times 100 = 34\%.$$

EXAMPLE 2

This example illustrates a second synthesis of acetic acid in high yield together with propionic acid and their esters directly from synthesis gas using a zirconium-ruthenium containing catalyst dispersed in tetrabutylphosphonium bromide salt (m.p. 100° C.).

A mixture of ruthenium(IV) oxide (4 mmoles) and bis(cyclopentadienyl)zirconium dichloride (4 mmoles) dispersed in tetrabutylphosphonium bromide (10.0 g) was charged to a glass liner, under nitrogen purge, and transferred to a 450 ml capacity pressure reactor equipped with heating and means of agitation. The reactor was sealed, flushed with $CO/H_2$ mixture and pressured to 4000 psig with a 1:1 molar $CO/H_2$ mixture. The mixture was heated to 220° C. with rocking, the pressure allowed to rise to ca. 7075 psig, and the reactor held at temperature for 18 hours.

On cooling, the reactor pressure (2725 psig) was noted, a typical gas sample taken and the excess gas removed. A dark-green liquid product (17.1 g) was recovered and samples were analyzed by glc and Karl Fischer titration and following results were obtained:
- 48.7 wt.% acetic acid
- 8.9 wt.% propionic acid
- 9.2 wt.% ethyl acetate
- 1.1 wt.% ethyl propionate
- 2.7 wt.% propyl propionate
- 1.6 wt.% water A small quantity of lighter, water-white, liquid phase was identified as primarily hydrocarbon.

Analysis of typical off-gas samples showed the presence of:
- 46% hydrogen
- 42% carbon monoxide
- 10% carbon dioxide
- 1.8% methane Since the total catalyst charge to the glass liner was 11.9 g, the yield of liquid products was calculated to be: 44%

Fractional distillation of a 7.3 g sample of the crude liquid product, under 0.1 mm Hg vacuum, produced a distillate sample comprising >80% purity acetic acid.

EXAMPLES 3-5

Following the general procedure of Example 1, three additional examples were run employing ruthenium(IV) oxide, ruthenium(III) acetylacetonate and triruthenium dodecacarbonyl coupled with the halide-containing titanium and zirconium salts, bis(cyclopentadienyl)titanium dichloride and bis(cyclopentadienyl)zirconium dichloride. The results obtained are set out in Table I, below. Acetic acid is a major product of CO hydrogenation in all three cases.

of 11.2 g of a brown solid. There was no liquid product in this case.

Pertinent data relating to these examples is shown in Table I.

EXAMPLE 8

A mixture of ruthenium(IV) oxide (4 mmoles) and zirconium(IV) bromide (4 mmoles) dispersed in tetrabutylphosphonium bromide (10.0 g) was charged to a glass liner, under nitrogen purge, and transferred to a 450 ml capacity pressure reactor equipped with heating and means of agitation. The reactor was sealed, flushed with $CO/H_2$ mixture and pressured to 4000 psig with a 1:1 molar $CO/H_2$ mixture. The mixture was heated to 220° C. with rocking, the pressure allowed to rise to ca. 5910 psig, and the reactor held at temperature for 18 hours.

On cooling the reactor pressure (1400 psig) was noted and the excess gas removed. The grey liquid product suspension (31.5 g) was recovered and samples analyzed by glc and Karl Fischer titration. Both acetic and propionic acids were identified as being present in the liquid product fraction.

EXAMPLE 9

A mixture of ruthenium chloride, hydrate (4.0 mmoles), bis(cyclopentadienyl)zirconium dichloride (4.0 mmoles), and tetrabutylphosphonium bromide (10 g), were charged to a glass liner, under $N_2$ purge, and transferred to the same 450 ml capacity pressure reactor as in Example I. The reactor was sealed, flushed with $CO/H_2$ mixture, pressured to 4000 psig with 1:1 molar $CO/H_2$ mixture and heated to 220° C. with rocking for 18 hours.

TABLE 1

| | | | Liquid Product Composition (Weight %)[b] | | | | | | | |
|---|---|---|---|---|---|---|---|---|---|---|
| Example[a] | Catalyst | Melt | HOAc | PrOOH | MeOAc | EtOAc/ MeOOPr | PrOAc/ EtOOPr | BuOOH/ PrOOPr | $H_2O$ | Liquid Yield (%) |
| 1 | $RuO_2$—$Cp_2ZrHCl$ | $Bu_4PBr$ | 45.3 | 3.2 | 0.8 | 9.6 | 5.6 | 3.3 | 1.9 | 34 |
| 2 | $RuO_2$—$Cp_2ZrCl_2$ | $Bu_4PBr$ | 48.7 | 8.9 | — | 9.2 | 1.1 | 2.7 | 1.6 | 44 |
| 3 | $RuO_2$—$Cp_2TiCl_2$ | $Bu_4PBr$ | 13.4 | 0.5 | 3.0 | 31.8 | 13.9 | 4.1 | 1.2 | 55 |
| 4 | $Ru(acac)_3$—$Cp_2ZrCl_2$ | $Bu_4PBr$ | 24.7 | 8.9 | 1.4 | 26.2 | 7.7 | 4.7 | 1.1 | 37 |
| 5 | $Ru_3(CO)_{12}$—$Cp_2ZrCl_2$ | $Bu_4PBr$ | 17.1 | 1.2 | 5.7 | 33.8 | 11.4 | 4.5 | 5.5 | 44 |
| 6 | $Cp_2ZrHCl$ | $Bu_4PBr$ | — | — | — | — | — | — | — | <5 |
| 7 | $Cp_2TiCl_2$ | $Bu_4PBr$ | — | — | — | — | — | — | — | <5 |

[a]Charge: Ruthenium, 4.0 mmoles; zirconium/titanium, 4.0 mmoles; tetrabutylphosphonium bromide, 10 g. Run Conditions: 4000 psig, 1:1 molar ($CO/H_2$), initial pressure.; 220° C., 18 hours.
[b]Designations: Acetic Acid (HOAc); Propionic Acid (PrOOH); Butyric Acid (BuOOH); Acetate Esters (MeOAc, EtOAc, PrOAc); Propionate Esters (MeOOPr, EtOOPr, PrOOPr).

COMPARATIVE EXAMPLES 6 and 7

In these comparative examples the catalyst utilized consisted only of the halide-containing titanium or zirconium compound dispersed in the low-melting quarternary. There was no ruthenium catalyst component in these examples. No liquid product was formed in the absence of the ruthenium component.

In a typical example (6), a mixture of bis(cyclopentadienyl)zirconium hydrochloride (4 mmoles) dispersed in tetrabutylphosphonium bromide (10 g) was charged to a glass liner, under $N_2$ purge, and transferred to a 450 ml capacity pressure reactor. The reactor was sealed, flushed with a $CO/H_2$ mixture, pressured to 400 psig with 1:1 molar $CO/H_2$ mixture and heated to 220° C. with rocking for 18 hours.

On cooling, the reactor pressure (4000 psig) was noted, a typical gas sample taken, and the excess gas removed. The product within the glass liner consisted On cooling, the reactor pressure (1020 psig) was noted and the excess gas removed. The dark-green liquid product suspension (32.6 g) was recovered and samples analyzed by glc and Karl Fischer titration. Acetic acid was identified as being present in this product liquid.

EXAMPLE 10

A mixture of ruthenium(IV) oxide (4 mmoles) and zirconium dichloride, oxide ($ZrCl_2O.4H_2O$, 4 mmoles) dispersed in tetrabutylphosphonium bromide (10.0 g) was charged to a glass liner, under nitrogen purge, and transferred to a 450 ml capacity pressure reactor equipped with heating and means of agitation. The reactor was sealed, flushed with $CO/H_2$ mixture and pressured to 4000 psig with a 1:1 molar $CO/H_2$ mixture. The mixture was heated to 220° C. with rocking, the pressure allowed to rise to ca. 6500 psig, and the reactor held at temperature for 18 hours.

On cooling the reactor pressure (1500 psig) was noted and the excess gas removed. A two-phase liquid product (20.2 g) was recovered and samples were analyzed by glc and Karl Fischer titration. The bulk of the product material consisted of a grey-colored heavier phase (15 ml) which contained both acetic acid (6.1%) and propionic acid (1.1%) fractions.

EXAMPLE 11

This example illustrates the synthesis of acetic acid together with propionic acid and their esters directly from synthesis gas using as catalyst a ruthenium-containing compound in combination with a halide-free zirconium compound plus elemental iodine.

A mixture of ruthenium oxide, hydrate (4.0 mmoles), zirconium(IV) 2,4-pentanedionate (4.0 mmoles), and tetrabutylphosphonium bromide (10 g), and elemental iodine (4.0 mmoles) were charged to a glass liner, under $N_2$ purge, and transferred to the same 450 ml capacity pressure reactor as in Example I. The reactor was sealed, flushed with $CO/H_2$ mixture, pressured to 4000 psig with 1:1 molar $CO/H_2$ mixture and heated to 220° C. with rocking for 18 hours.

On cooling, the reactor pressure (1350 psig) was noted and the excess gas removed. The product within the glass liner consisted of 29.9 g of a grey-green colored slurry.

Analysis of typical liquid samples showed the presence of:
15.1 wt.% acetic acid
4.4 wt.% propionic acid
1.0 wt.% methyl acetate
72.2 wt.% water

What is claimed is:

1. A process for making acetic and propionic acids and their esters which comprises contacting a mixture of CO and $H_2$ at a pressure of about 500 psig or greater and at a temperature of at least about 150° C. with a catalyst system comprising a ruthenium-containing compound and a material selected from the group consisting of a halogen-containing titanium salt and a halogen-containing zirconium salt dispersed in a low melting quaternary phosphonium or ammonium base or salt.

2. The process of claim 1 wherein the process is conducted at a pressure of about 500 psig to about 9000 psig.

3. The process of claim 1 wherein the process is conducted at a temperature of about 150° to about 350° C.

4. The process of claim 1 wherein the process is conducted at a temperature of about 180° to about 250° C.

5. The process of claim 1 wherein the said material is a halogen-containing titanium compound.

6. The process of claim 5 wherein the said halogen-containing titanium salt is selected from the group consisting of bis(cyclopentadienyl)titanium dichloride, bis(cyclopentadienyl)titanium hydrochloride, titanium(IV) chloride, and titanium(IV) bromide.

7. The process of claim 6 wherein said halogen-containing titanium salt is bis(cyclopentadienyl)titanium dichloride.

8. The process of claim 1 wherein the said material is a halogen-containing zirconium salt.

9. The process of claim 8 wherein the said halogen-containing zirconium salt is selected from the group consisting of bis(cyclopentadienyl)zirconium dichloride, bis(cyclopentadienyl)zirconium hydrochloride, zirconium(IV) chloride, zirconium(IV) bromide and zirconium dichloride, oxide.

10. The process of claim 9 wherein said halogen-containing zirconium salt is bis(cyclopentadienyl)zirconium hydrochloride.

11. The process of claim 9 wherein said halogen-containing zirconium compound is bis(cyclopentadienyl)zirconium dichloride.

12. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

13. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium(III) propionate, ruthenium(III) acetylacetonate and triruthenium dodecarbonyl.

14. The process of claim 1 wherein said ruthenium-containing compound is ruthenium(IV) dioxide.

15. The process of claim 1 wherein said ruthenium-containing compound is ruthenium(III) acetylacetonate.

16. The process of claim 1 wherein said quaternary salt or base has a melting point less than about 180° C.

17. The process of claim 1 wherein said quaternary salt is a tetraalkylphosphonium salt.

18. The process of claim 17 wherein said alkyl groups contain 1-6 carbon atoms.

19. The process of claim 1 wherein said quaternary salt is tetrabutylphosphonium salt.

20. The process of claim 1 wherein said quaternary salt is a mixed alkylaryl phosphonium quaternary salt.

21. The process of claim 1 wherein said quaternary phosphonium base is tetrabutylphosphonium hydroxide.

22. The process of claim 1 wherein said quaternary phosphonium salt is tetrabutylphosphonium bromide.

23. A process for making acetic and propionic acids and their esters which comprises contacting a mixture of CO and $H_2$ at a pressure of about 500 psig or greater and at a temperature of at least about 150° C. with a catalyst system comprising a ruthenium-containing compound and a material selected from the group consisting of a halogen-free titanium compound and a halogen-free zirconium compound together with an iodide- or iodine-containing compound dispersed in a low melting quaternary phosphonium or ammonium base or salt.

24. The process of claim 23 wherein the said material is a halogen-free titanium compound.

25. The process of claim 24 wherein the said titanium compound is selected from the group consisting of titanium(IV) 2,4-pentanedionate, titanium(IV) methoxide and titanium oxide.

26. The process of claim 23 wherein the said material is a halogen-free zirconium compound.

27. The process of claim 26 wherein the said zirconium compound is selective from the group consisting of zirconium(IV) 2,4-pentanedionate, zirconium(IV) methoxide and zirconium diacetate oxide.

28. The process of claim 23 wherein the said catalyst system includes an iodine-containing compound.

29. The process of claim 28 wherein the said iodine-containing compound is elemental iodine.

30. The process of claim 23 wherein the said catalyst system includes an iodine-containing compound.

31. The process of claim 30 wherein the said iodide-containing compound is an alkyl iodide.

32. The process of claim 30 wherein said iodide-containing compound is methyl iodide.

* * * * *